US00PP37834P2

(12) United States Plant Patent
Masvidal

(10) Patent No.: US PP37,834 P2
(45) Date of Patent: Nov. 3, 2026

(54) ***LAVANDULA* PLANT NAMED 'ST21-53'**

(50) Latin Name: *Lavandula stoechas*
Varietal Denomination: ST21-53

(71) Applicant: Plantinova SL, Cabrils (ES)

(72) Inventor: Luis Masvidal, Cabrils (ES)

(73) Assignee: Plantinova SL (ES)

( * ) Notice: Subject to any disclaimer, the term of this patent is extended or adjusted under 35 U.S.C. 154(b) by 0 days.

(21) Appl. No.: 19/395,284

(22) Filed: Nov. 20, 2025

(51) Int. Cl.
*A01H 5/02* (2018.01)
*A01H 6/50* (2018.01)

(52) U.S. Cl.
USPC ..... Plt./445

(58) Field of Classification Search
USPC ..... Plt./445
CPC . A01H 5/02; A01H 5/00; A01H 6/502; A01H 6/50
See application file for complete search history.

(56) References Cited

U.S. PATENT DOCUMENTS

PP20,068 P2 * 6/2009 Koning ..... A01H 5/02 Plt./226

* cited by examiner

*Primary Examiner* — June Hwu

(57) ABSTRACT

A new and distinct cultivar of *Lavandula stoechas* plant named 'ST21-53' is disclosed, characterized by silver foliage and dusky purple flowers. Plants are dense and rounded with uniform flowering. The new cultivar is a *Lavandula,* typically produced as an outdoor ornamental plant.

2 Drawing Sheets

Latin name of the genus and species: *Lavandula stoechas.*
Variety denomination: 'ST21-53'.

BACKGROUND OF THE INVENTION

A product of a planned breeding program conducted by the inventor, Cabrils, Spain. The objective of the breeding program was to produce new *Lavender* varieties for ornamental commercial applications. The open pollination resulting in this new variety was made during 2017.

A breeding block of more than 50 different unpatented, unnamed proprietary *Lavandula stoechas* was organized for cross pollination, with the resulting seed bulk collected. The new variety was selected in July of 2020 by the inventor in a group of seedlings resulting from this cross-pollination. Exact parents cannot be identified.

Asexual reproduction of the new cultivar was performed by vegetative terminal cuttings. This was first performed at a research greenhouse in Cabrils, Spain during October of 2020 and has shown that the unique features of this cultivar are stable and reproduced true to type in at least 2 successive generations.

SUMMARY OF THE INVENTION

The cultivar 'ST21-53' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ST21-53' These characteristics in combination distinguish 'ST21-53' as a new and distinct *Lavandula* cultivar:

1. Silver foliage.
2. Dusky purple flowers.

3. Uniform flowering.
4. Dense, rounded plant.

The parents cannot be identified for comparison.

COMMERCIAL COMPARISON

Plants of the new cultivar 'ST21-53' are comparable to the variety *Lavandula* 'Madrid Purple', unpatented. The two *Lavandula* varieties are similar in most horticultural characteristics; however, the new variety 'ST21-53' differs in producing plants which are more dense with more lateral branches. Additionally foliage color of the new cultivar is silver compared to the green foliage color of 'Madrid Purple'. Flower color of the new cultivar is more violet and purple than the red-purple of 'Madrid Purple'.

Plants of the new cultivar 'ST21-53' are comparable to the variety *Lavandula* 'Silver Anouk', U.S. Plant Pat. No. 20,068. The two *Lavandula* varieties are similar in most horticultural characteristics; however, the new variety 'ST21-53' differs in producing a rounder plant with about 50% more lateral branches. Petal of the new cultivar are colored Violet 83A; petals of this comparator are colored various shades of Violet-Blue. Foliage color of the new cultivar is Greyed-Green 188B (light greenish grey); foliage color of this comparator is Greyed-Green 191A (greyish yellow green).

BRIEF DESCRIPTION OF THE PHOTOGRAPHS

Figure 1:
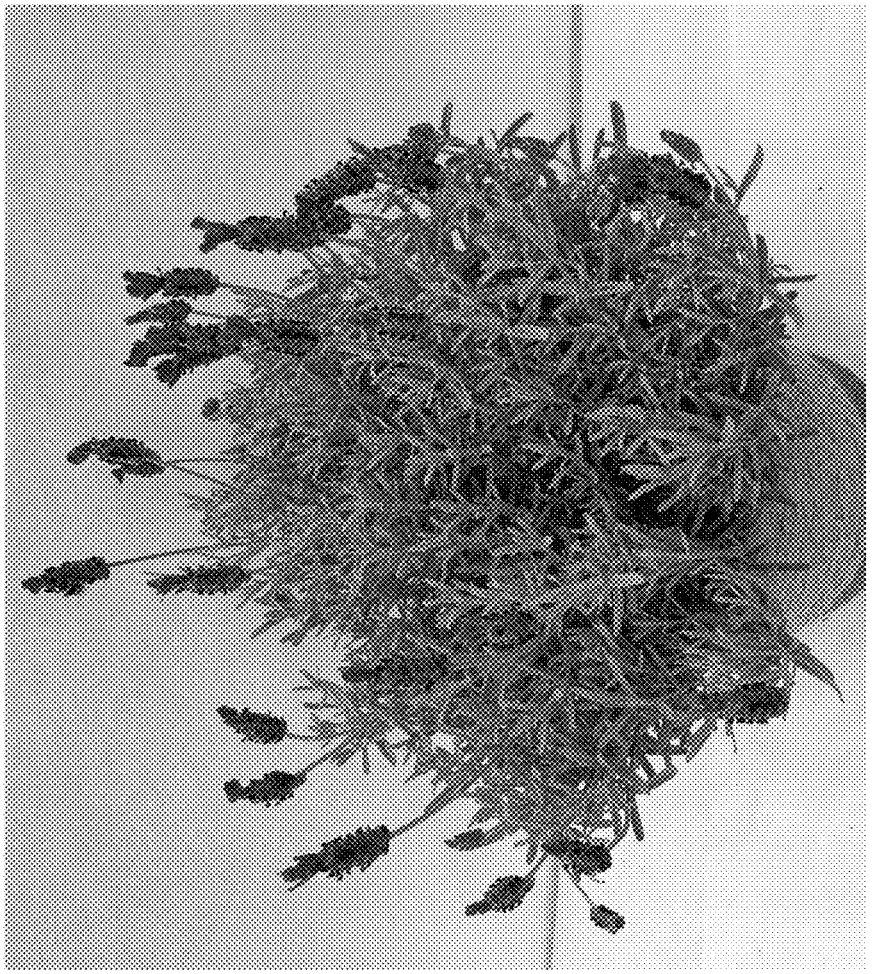

The accompanying photographs in FIG. 1 illustrates in full color a typical plant of 'ST21-53' grown outdoors in Denmark. This plant was photographed during September, having a lesser flush of flowers than in Spring. Age of the plant photographed is approximately one-year from a rooted cutting.

Figure 2:
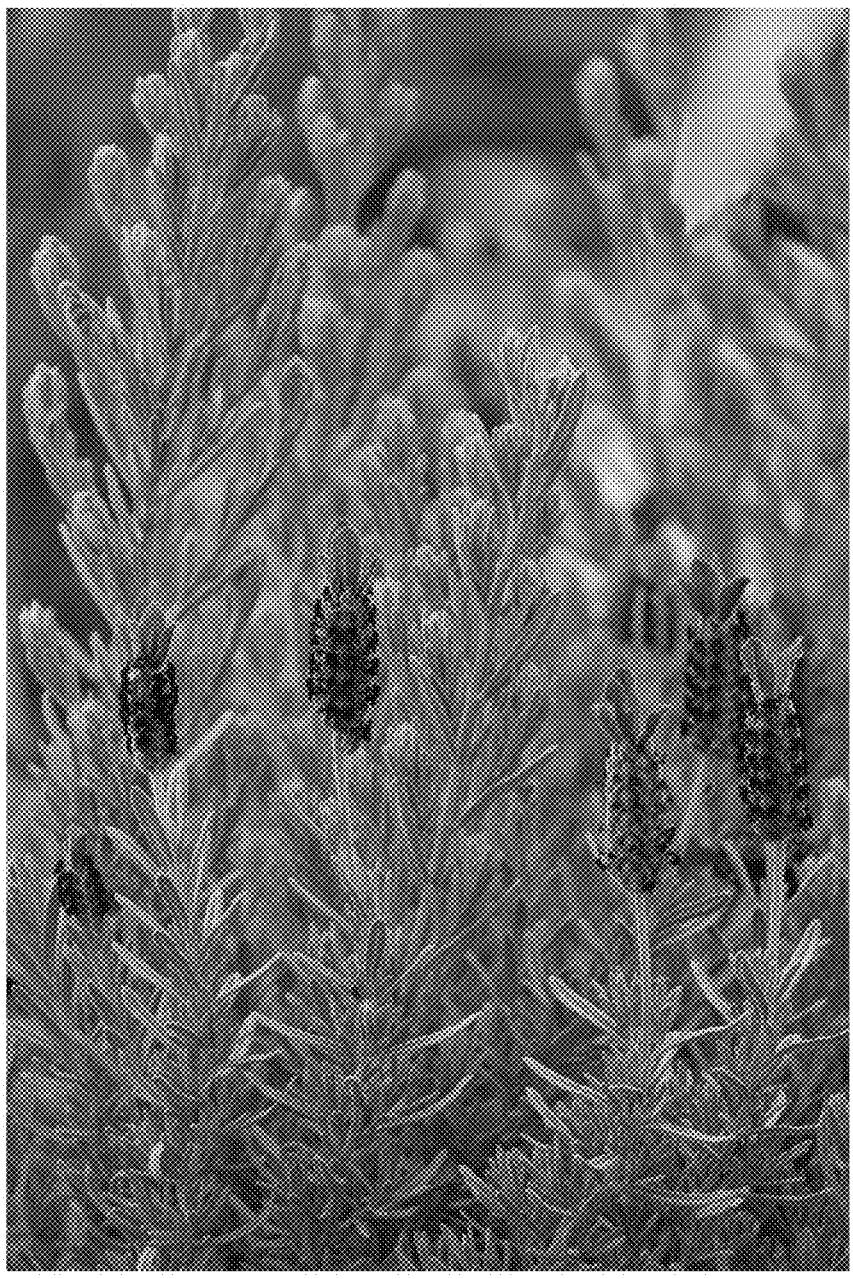

FIG. 2 is a close-up view of the foliage and inflorescences.

The photographs were taken using conventional techniques and although colors may appear different from actual colors due to light reflectance are as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'ST21-53' plants grown outdoors during Summer in California. The growing temperature ranged from about 10° C. to 35° C. during the day and from about 5°° C. to 25° C. during the night. General light conditions are bright, normal sunlight. Measurements and numerical values represent averages of typical plant types.

Botanical classification: *Lavandula stoechas* 'ST21-53'.

PROPAGATION

Time to initiate roots: About 10 to 14 days at approximately 21° C.

Time to produce a rooted cutting: About 25 to 35 days at 21° C.

Root description: Well-branched woody main roots expending into fine, fibrous secondary roots. Older roots colored near grey-Brown N199B. Younger roots colored near Grey-Brown 199D and White 155A.

PLANT

Age of plant described: Approximately 12 months from an unrooted cutting.

Plant habit: Dense, rounded flowering perennial.

Plant shape: Round.

Plant spread: Approximately 50 cm.

Plant height: Approximately 42 cm.

Quantity of primary branches: 10 to 18.

Length of primary branches: Approximately 15 to 28 cm.

Diameter of branches: Approximately 9 to 12 mm.

Texture of primary branches: Scaly.

Color of primary branches: Greyed-Purple 187A covered in streaks of N187C and 187D.

Quantity of lateral branches: 40 to 55.

Length of lateral branches: 12 to 20 cm.

Diameter of lateral branches: 5 mm.

Lateral branch color: Mature: Greyed-Green 188A. New Growth: Greyed-Green 188D flushed Greyed-Purple N187B and N187C.

Internode length: Average Range 1.2 to 3.0 cm.

FOLIAGE

Leaf:

*Arrangement.*—2 opposite leaves at each node.

*Leaf type.*—Simple.

*Quantity.*—Average 40 to 80 per main branch.

*Average length.*—2.2 to 2.7 cm.

*Average width.*—4 mm.

*Shape of blade.*—Lanceolate.

*Apex.*—Acute.

*Base.*—Truncate.

*Attachment.*—Sessile.

*Margin.*—Entire.

*Texture of all surfaces.*—Puberbulent.

*Leaf fragrance.*—Typical Lavender scent. Moderate strength.

*Color.*—Young foliage upper side: R.H.S. Greyed-Green 188C. Young foliage under side: R.H.S. Greyed-Green 188C. Mature foliage upper side: R.H.S. Greyed-Green 188B. Mature foliage under side: R.H.S. Greyed-Green 188B.

*Venation.*—Type: Reticulate. Venation color upper side: Indistinguishable from foliage color. Venation color under side: Indistinguishable from foliage color.

*Petiole.*—Absent.

FLOWER

Bloom period: Main flush during Spring. Additional flowering produced throughout Summer and Fall.

Inflorescence:

*Form.*—Small single flower in verticillasters arranged in spikes. 6 to 8 rows of flowers, each row typically having 6 to 8 flowers. Flowers have small bracts, and large showy terminal bracts. Number of individual flowers per spike: Average 40 to 50.

*Inflorescences per plant.*—Average 30 at one time.

*Fragrance.*—Moderately strong lavender scent.

*Inflorescence Size, excluding terminal bracts.*—Length: Approximately 4 cm. Width: Approximately 1.8 cm. Shape: Cylindrical.

Individual flower:

*Corolla shape.*—Salverform. Depth: About 4 mm. Diameter: About 5 mm. Throat Diameter: About 2 mm. Texture: Glabrous all surfaces. Tube Length: 4 mm. Tube Diameter: 2 mm. Tube Texture: Glabrous all surfaces. Tube Color: Exterior near Violet-Blue N92A. Interior near Violet-Blue N92D. Flower Lastingness: About 4 weeks.

Petals:

*Petal number.*—5. Petals Fused or Unfused: Fused at base. Petal Shape: Top 2 lobes obovate, lower 3 lobes ovate. Petal Margin: Entire. Petal Surfaces: Glabrous. Length: Approximately 3 mm. Diameter: Approximately 4 mm at widest opening of petals.

*Petal coloration.*—Immature: Violet-Blue N92A upper and lower surfaces. Mature: Violet 83A upper and lower surfaces.

Calyx:

*Calyx width.*—3 mm.

*Calyx length.*—4 mm.

*Calyx shape.*—Flattened tube.

*Calyx color.*—R.H.S. Greyed-Purple N187C, flushed N187B.

Basal floral bracts:

*Quantity.*—1 per individual flower.

*Bract shape.*—Broad deltoid.

*Bract apex.*—Acute.

*Margin.*—Entire.

*Base.*—Broadly tapered.

*Texture.*—Softly and densely pubescent lower surfaces. Upper surface moderately pubescent.

*Lastingness.*—Bracts non-desiccated for approximately 4 weeks.

*Bract color.*—Lower Surface: Greyed-Green 188B, flushed N187C. Upper Surface: Greyed-Green 188B, flushed N187C.

Terminal bracts (sterile):

*Quantity.*—4 to per inflorescence.

*Attitude and angle of attachment.*—Bracts either completely upright, or at a 15 degree angle from the top of the inflorescence.

*Length.*—Approximately 2 cm.

*Width.*—Approximately 9 mm.

*Form.*—Petaloid.

*Margin.*—Entire and very slightly undulating.

*Texture.*—Smooth all surfaces.

*Appearance.*—Matte.

*Shape.*—Oblanceolate.

*Apex.*—Acute.

*Base.*—Attenuate.

*Vein pattern.*—Reticulate.

*Duration on plant.*—Approximately 12 weeks, with good color. Persistent.

*Color.*—Upper side of immature bract: Purple N79D flushed Purple-Violet N81A, veins Greyed-Green 188C. Under side of immature bract: Purple N79D flushed Purple-Violet N81A, veins Greyed-Green 188C. Upper side of mature bract: Purple-Violet N81D flushed Purple-Violet N81B, veins Greyed-Green 188C. Under side of mature bract: Purple-Violet N81D flushed Purple-Violet N81B, veins Greyed-Green 188C.

Bud:

*Length.*—Approximately 5 mm.

*Diameter.*—Approximately 5 mm.

*Shape.*—Ovate.

*Color.*—Purple N79A. Rate of Opening: Varies with climactic conditions; Approximately 1 week from colored bud to open flower.

Peduncle:

*Peduncle length.*—Average range 3 to 4 cm.

*Peduncle diameter.*—Approximately 4 mm.

*Aspect.*—Straight.

*Color.*—Greyed-Green 189C.

*Texture.*—Softly and densely pubescent.

REPRODUCTIVE ORGANS

Androecium: Extremely reduced, frequently not present.

*Stamens.*—4.

*Anther shape.*—Linear.

*Anther length.*—Approximately 0.5 mm.

*Anther color.*—Purple N79A.

*Pollen quantity.*—Pollen production not observed.

Pistil:

*Number.*—1.

*Length.*—Approximately 3 mm.

*Style.*—Length: Approximately 0.2 cm. Color: Purple N79D.

*Stigma.*—Shape: Globular. Color: Purple N79B. Ovary: Minute and immeasurable.

OTHER CHARACTERISTICS

Seeds and fruits: Seed production not observed to date.

Disease/pest resistance: Neither resistance nor susceptibility to the normal diseases and pests of *Lavandula stoechas* has been observed.

Drought tolerance and cold tolerance: Hardy perennial. Tolerates high temperature to at least 32° C. Tolerates low temperatures to −5° C. While specific drought tolerance has not been observed, once plants are established very little water is necessary to maintain plants.

What is claimed is:

1. A new and distinct cultivar of *Lavandula* plant named 'ST21-53' as herein illustrated and described.

* * * * *